(12) United States Patent
Sarfarazi

(10) Patent No.: US 6,207,394 B1
(45) Date of Patent: Mar. 27, 2001

(54) DIAGNOSIS OF PRIMARY CONGENITAL GLAUCOMA

(75) Inventor: Mansoor Sarfarazi, New Britain, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 09/605,223

(22) Filed: Jun. 28, 2000

Related U.S. Application Data

(62) Division of application No. 09/307,402, filed on May 7, 1999, now Pat. No. 6,127,128.

(51) Int. Cl.[7] .............................. G01N 33/53; C12Q 1/68; A61K 38/00
(52) U.S. Cl. .................................. 435/7.1; 435/6; 514/2; 530/356
(58) Field of Search ........................... 435/7.1, 6; 514/2; 530/350

(56) References Cited

U.S. PATENT DOCUMENTS

| | | | |
|---|---|---|---|
| 5,885,776 | 3/1999 | Stone et al. | 435/6 |
| 5,916,778 | 6/1999 | Stone et al. | 435/91.2 |
| 5,925,748 | 7/1999 | Stone et al. | 536/23.1 |

FOREIGN PATENT DOCUMENTS

| | | |
|---|---|---|
| WO96/14411 | 5/1996 | (WO) . |
| WO96/33287 | 10/1996 | (WO) . |

OTHER PUBLICATIONS

Leff, D.N., "New-Found Gene Enables Testing Infants for Inherited Blindness Disease", *BioWorld Today*, 8(53):1 (Mar. 19, 1997).

Stone, E.M., et al., "Identification of a Gene That Causes Primary Open Angle Glaucoma", *Science*, 275:668–670 (1997).

Vogel, G., "Glaucoma Gene Provides Light at the End of the Tunnel", Science, 275:621 (1997).

Stoilova, D., et al., "Localization of a Locus (GLC1B) for Adult–Onset Primary Open Angle Glaucoma to the 2cen–q13 Region", *Genomics*, 36:142–150 (1996).

Sarfarazi, M., et al., "Assignment of a Locus (GLC3A) for Primary Congenital Glaucoma (Buphthalmos) to 2p21 and Evidence for Genetic Heterogeneity", *Genomics*, 30:171–177 (1995).

Akarsu, A.N., et al., "A Second Locus (GLC3B) for Primary Congenital Glaucoma (Buphthalmos) Maps to the 1p36 Region", *Human Molecular Genetics*, 5(8):1199–1203 (1996).

Akarsu, A.N., et al., "Exclusion of Primary Congenital Glaucoma (Buphthalmos) From Two Candidate Regions of Chromosome Arm 6p and Chromosome 11", *American Journal of Medical Genetics*, 61:290–292 (1996).

Stoilov, I., et al., "Fine Mapping of Primary Congenital Glaucoma (Buphthalmos) on 2p21 and Mutation Screening of Candidate Genes," *Am. J. Hum. Genet.* (Supplement) 59(3): Abstract No. 1366, p. A237 (1996).

Yilmaz, E., "Localization and Mutation Screening of a New Locus (GLC3B) for Primary Congenital Glaucoma (Buphthalmos) on 1p36," *Am. J. Hum. Genet.* (Supplement) 59(3): Abstract No. 1404, p. A243 (1996).

Stoilova, D., et al., "Assignment of a New Locus (GLC1B) for Adult–Onset Primary Open Angle Glaucoma to the 2cen–q13 Region," *Am. J. Hum. Genet.* (Supplement) 59(3): Abstract No. A1407A, p. A244 (1996).

Bejjani, B.A., et al., "Mapping Strategies in Primary Congenital Glaucoma (PCG)," *Am. J. Hum. Genet.* (Supplement) 59(3): Abstract No. 1216, p. A212 (1996).

Wiggs, J.L., et al., "The juvenile glaucoma gene on 1q21–q31 is not associated with adult–onset primary open angle glaucoma," *Am. J. Hum. Genet.* (Supplement) 59(3): Abstract No. 1393, p. A242 (1996).

Allingham, R.R., et al., "Genes linked to systemic hypertension (HTN) and non–insulin dependent diabetes mellitus (NIDDM) are not associated with primary open angle," *Am. J. Hum. Genet.* (Supplement) 59(3): Abstract No. 2213, p. A380 (1996).

Raymond, V., et al., "Homozygotes for autosomal dominant open–angle glaucoma at the GLC1A locus," *Am. J. Hum. Genet.* (Supplement) 59(3): Abstract No. 1625, p. A280 (1996).

Richards, J.E., et al., "Juvenile glaucoma linked to GLC1A in a family of spanish origin," *Am. J. Hum. Genet.* (Supplement) 59(3): Abstract No. 2257, p. A387 (1996).

Booth, A.P., et al., "Physical and genetic mapping of the juvenile–onset primary open–angle glaucoma locus," *Am. J. Hum. Genet.* (Supplement) 59(3): Abstract No. 2359, p. A404 (1996).

Suden, S.L.F., et al., "Narrowing the GLC1A critical region using a late–onset autosomal dominant open angle glaucoma family," *Am. J. Hum. Genet.* (Supplement) 59(3): Abstract No. 1369, p. A238 (1996).

Graff, C. et al., "Confirmation of Linkage to 1q21–31 in a Danish Autosomal Dominant Juvenile–Onset Glaucoma Family and Evidence of Genetic Heterogeneity", *Human Genet.*, 96:285–289 (1995).

(List continued on next page.)

*Primary Examiner*—Jeffrey Fredman
*Assistant Examiner*—Juliet C Einsmann
(74) *Attorney, Agent, or Firm*—Hamilton, Brook, Smith & Reynolds, P.C.

(57) ABSTRACT

Methods of diagnosing primary congenital glaucoma, by detecting particular mutations in a human cytochrome P4501B1 (CYP1B1) gene, are disclosed. Methods include hybridization analysis, such as Southern or Northern analysis, which use hybridization of a mutant nucleic acid probe to the CYP1B1 gene; direct mutation analysis by restriction digest; sequencing of the CYP1B1 gene; hybridization of an allele-specific oligonucleotide with amplified genomic DNA; or identification of the presence of mutant proteins encoded by the CYP1B1 gene.

1 Claim, No Drawings

OTHER PUBLICATIONS

Morissette, J., et al., "A Common Gene for Juvenile and Adult Onset Primary Open–Angle Glaucoma Confines on Chromosone 1q", *Am. J. Hum. Genet.*, 56:1431–1442 (1995).

Richards, J.e. et al., "Mapping of a Gene for Autosomal Dominant Juvenile–Onset Open–Angle Glaucoma to Chromosone 1Q," am. J. Hum. Genet., 54:62–70 (1994).

Seghatoleslami, M.R., et al., "Fine Mapping of Juvenile Primary Open Angle Glaucoma (POAG) on 1q21–q31 and Exclusion of Adult–POAG from the Respective Region", *Am. J. Hum. Genet.*, 55:Abtract 1179, pp. A203 (1994).

Seghatoleslami, M.R., et al., "Exclusion Mapping of the Adult–Onset Primary Open–Angle Glaucoma (POAG)", *Invest. Ophthalmol. & Visual Science*, 36(4): Abstract 4792, pp. S1034 (1995).

Sheffield, V.C. et al., "A Collection of Tri–and Tetranucleotide Repeat Markers Used to Generate High Quality, High Resolution Human Genomewide Linkage Maps," *Hum. Mol. Genet.*, 4:1837–1844 (1995).

Stoilova, D., et al., "Genetic Linkage Study of Adult–Onset Primary Open Angle Glaucoma", *Am. J. Hum. Genet.*, 57(4):Abstract 1895, pp. A326 (1995).

Wiggs, J.L. et al., "Clinical Features of Five Pedigrees Genetically Linked to the Juvenile Glaucoma Locus on Chromosome 1q21–q31", *Ophthalmology*, 102:1782–1789 (1995).

Wiggs, J.L. et al., "Genetic Linkage of Autosomal Dominant Juvenile Glaucoma to 1q21–q31 in Three Affected Pedigrees", *Genomics*, 21:299–303 (1994).

Sutter, T.R. et al., "Complete cDNA Sequence of a Human Dioxin–Inducible mRNA Identifies a New Gene Subfamily of Cytochrome P450 That Maps to Chromosome 2", *J. Biol. Chem.* 269:13092–13099 (1994).

Sarfarazi, M., "Recent Advances in Molecular Genetics of Glaucomas," *Hum. Mol. Genet.*, 6(10):1667–1677 (1997).

Stoilov, I., et al., "Identification of Three Different Truncating Mutations in Cytochrome P4501B1 (CYP1B1) as the Principal Cause of Primary Congenital Glaucoma (Buphthalmos) in Families Linked to the GLC3A Locus on Chromosome 2p21," *Hum. Mol. Genet.*, 6(4): 641–647 (1997).

Stoilova, D., et al., "Identification of a New 'TIGR' Mutation in a Family with Juvenile–Onset Primary Open Angle Glaucoma", *Opthal. Genet.*, 18:109–118 (1997).

Ming, Y.T., et al., "Isolation and Characterization of the Human Cytochrome P450 CYP1B1 Gene," *J. Biol. Chem.* 271(45):28324–28330 (1996).

Bejjani, B.A., et al., "Mutations in CYP1B1, the Gene for Cytochrome P4501B1, Are the Predominant Cause of Primary Congenital Glaucoma in Saudi Arabia," *Am. J. Hum. Genet.* 62:325–333 (1998).

Stoilov, I., et al., "Identification of 11 New CYP1B1 Mutations in Primary Congenital Glaucoma", *IVOS*, Mar. 15, 1999 vol. 40 (4), Abstract.

DIAGNOSIS OF PRIMARY CONGENITAL GLAUCOMA

RELATED APPLICATION

This application is a Divisional of U.S. Ser. No. 09/307,402, filed on May 7, 1999, now U.S. Pat. No. 6,127,128 which is incorporated by reference in its entirety.

GOVERNMENT FUNDING

This invention was made with Government support under Contract No. EY-11095 awarded by the National Eye Institute and Contract No. MOI-RR-06192 awarded by the National Institutes of Health. The Government has certain rights in the invention.

BACKGROUND OF THE INVENTION

Glaucoma is a group of ocular disorders, characterized by degeneration of the optic nerve. It is one of the leading causes of blindness worldwide. One major risk factor for developing glaucoma is family history: several different inherited forms of glaucoma have been described.

Primary congenital or infantile glaucoma (gene symbol:GLC3) is an inherited disorder that accounts for 0.01–0.04% of total blindness. It is characterized by an improper development of the aqueous outflow system of the eye, which leads to elevated intraocular pressure, enlargement of the globe or cornea (i.e., buphthalmos), damage to the optic nerve, and eventual visual impairment. Pathogenesis of GLC3 remains elusive despite efforts to identify a single anatomic defect. At least two chromosomal locations associated with the disease have been identified: one locus at 2p21 (GLC3A) (Sarfarazi, M. el al., Genomics 30:171–177 (1995); and a second locus at 1p36 (GLC3B) (Akarsu, A. N. et al., Hum. Mol. Gen. 5(8):1199–1203 (1996)). Other specific loci, including a region of 6p and chromosome 11, have been excluded (Akarsu, A. N. et al., Am. J. Med. Genet. 61:290–292 (1996)).

Primary open angle glaucoma (gene symbol: GLC1) is a common disorder characterized by atrophy of the optic nerve resulting in visual field loss and eventual blindness. GLC1 has been divided into two major groups, based on age of onset and differences in clinical presentation.

Juvenile-onset primary open angle glaucoma (GLC1A) usually manifests in late childhood or early adulthood. The progression of GLC1A is rapid and severe with high intraocular pressure, is poorly responsive to medical treatment, and is such that it usually requires ocular surgery. GLC1A was initially mapped to the q21–q31 region of chromosome 1 (Sheffield, V. C. et al., Hum. Mol. Genet. 4:1837–1844 (1995)); mutations in the gene for trabecular meshwork inducible glucocorticoid response (TIGR) protein, located a chromosome 1q24, have been identified as associated with GLC1A glaucoma (Stone, E. M. et al., Science 275:668–670 (1997); Stoilova, D. et al., Opthamalic Genetics 18(3):109–118 (1997); Adam, M. F. et al., Hum. Mol. Genet. 6:2091–2097 (1997); Michels-Rautenstrauss, K. G., et al., Hum. Genet. 102:103–106 (1998); Mansergh, F. C. et al., Hum. Mutat. 11:244–251 (1998)).

Adult- or late-onset primary open angle glaucoma (GLC1B) followed by direct mutation analysis by restriction enzyme digestion is the most common type of glaucoma. It is milder and develops more gradually than juvenile-onset primary open angle glaucoma, with variable onset usually after the age of 40. GLC1B is associated with slight to moderate elevation of intraocular pressure, and often responds satisfactorily to regularly monitored medical treatment. However, because the disease progresses gradually and painlessly, it may not be detected until a late stage when irreversible damage to the optic nerve has already occurred. Linkage, haplotype and clinical data have assigned a locus for GLC1B to the 2cen-q13 region as well as a new locus 3q21-q22 (Stoilova, D. et al., Genomics 36:142–150 (1996)). Further evidence has identified several additional loci for primary open angle glaucoma. GLC1C, an adult-onset POAG gene, has been mapped to 3q (Wirtz, M. K. et al., Am. J. Hum. Genet. 60:296–304 (1997)); GLC1D has been mapped to 8q23 (Trifan, O. C. et al., Am. J Ophthalmol. 126:17–28 (1998)); GLC1E has been mapped to 10p15-p14 (Sarfarazi, M. et al., Am. J Hum. Genet. 62:641–652 (1998)).

Because of the insidious nature of glaucoma, a need remains for a better and earlier means to diagnose or predict the likelihood of development of glaucoma, so that preventative or palliative measures can be taken before significant damage to the optical nerve occurs.

SUMMARY OF THE INVENTION

The invention pertains to methods of diagnosing primary congenital glaucoma, by detecting the presence of certain mutations in the human cytochrome P4501B1 gene (CYP1B1 gene). The mutations include a single-base change (a T→C transition) in codon 1, resulting in a change of the encoded amino acid (the initiation codon (Met1)) to Thr; a single-base change (a G→A transition) in codon 57, resulting in a change of the encoded amino acid from Trp57 to a stop codon; a single-base change (a C→A transition) in codon 65, resulting in a change of the encoded amino acid from Ala65 to Glu; a single-base change (a T→A transition) in codon 81, resulting in a change of the encoded amino acid from Tyr81 to Asn; a single-base change (a T→G transition) in codon 137, resulting in a change of the encoded amino acid from Tyr137 to Asp; a single-base change (a G→C transition) in codon 238, resulting in a change of the encoded amino acid from Gly238 to Arg; a single-base change (a G→C transition) in codon 242, resulting in a change of the encoded amino acid from Asp242 to His; a single-base change (a C→A transition) in codon 261, resulting in a change of the encoded amino acid from Phe261 to Leu; a single-base change (a T→G transition) in codon 356, resulting in a change of the encoded amino acid from Val356 to Gly; a single-base change (a G→A transition) in codon 368, resulting in a change of the encoded amino acid from Arg368 to His; a single-base change (a C→T transition) in codon 390, resulting in a change of the encoded amino acid from Arg390 to Cys; a single-base change (a G→A transition) in codon 393, resulting in a change of the encoded amino acid from Ser393 to Asn; a single-base change (a C→T transition) in codon 400, resulting in a change of the encoded amino acid from Pro400 to Ser; a single-base change (a C→G transition) in codon 443, resulting in a change of the encoded amino acid from Ala443 to Gly; a single-base change (a T→A transition) in codon 445, resulting in a change of the encoded amino acid from Phe445 to Ile; a single-base change (a T→C transition) in codon 464, resulting in a change of the encoded amino acid from Ser464 to Pro; a deletion of nucleotide 4340 (G); a deletion of nucleotide 4634 (T); a deletion of nucleotide 4681 (G); a deletion of nucleotide 8228 (C); and a deletion of nucleotides 8373–8378.

More than one of these mutations can be present in the CYP1B1 gene. The mutations can be identified by numerous methods, such as Southern analysis of genomic DNA;

amplification of genomic DNA followed by direct mutation analysis by restriction enzyme digestion; Northern analysis of RNA; gene isolation and direct sequencing; or analysis of the CYP1B1 protein.

For example, a sample of DNA containing the CYP1B1 gene is obtained from an individual suspected of having primary congenital glaucoma or of being a carrier for primary congenital glaucoma (the test individual). The DNA is contacted with at least one mutant nucleic acid probe under conditions sufficient for specific hybridization of the CYP1B1 gene to the mutant nucleic acid probe. The mutant nucleic acid probe comprises DNA, cDNA, or RNA of the gene, or a fragment of the gene, having at least one of the mutations described above, or an RNA fragment corresponding to such a cDNA fragment. The presence of specific hybridization of the gene to the mutant nucleic acid probe is indicative of a mutation that is associated with primary congenital glaucoma. In another example, the DNA is contacted with a PNA probe under conditions sufficient for specific hybridization of the gene to the PNA probe; the presence of specific hybridization is indicative of a mutation that is associated with primary congenital glaucoma.

Alternatively, direct mutation analysis by restriction digest of a sample of genomic DNA, RNA or cDNA from the test individual can be conducted, if the mutation results in the creation or elimination of a restriction site. The digestion pattern of the relevant DNA, RNA or cDNA fragment indicates the presence or absence of the mutation associated with primary congenital glaucoma.

The presence of a mutation associated with primary congenital glaucoma can also be diagnosed by sequence data. A sample of genomic DNA, RNA or cDNA from the test individual is obtained, and the sequence of the CYP1B1 gene, or a fragment of the gene, is determined. The sequence of the CYP1B1 gene from the individual is compared with the known sequence of the CYP1B1 gene (the control sequence). The presence of a mutation as described above in the gene of the individual is indicative of the presence of a mutation that is associated with primary congenital glaucoma.

The invention additionally pertains to methods of diagnosing primary congenital glaucoma in an individual by detecting alterations in the composition of the protein encoded by the CYP1B1 gene. An alteration in the composition of the CYP1B1 protein is indicative of the disease. Alterations in composition of the protein can be assessed using standard techniques, such as Western blotting.

The invention additionally pertains to antibodies (monoclonal or polyclonal) to proteins encoded by CYP1B1 genes having the mutations described above. These antibodies can also be used in methods of diagnosis. For example, a test sample which includes CYP1B1 protein of interest is contacted with antibodies specific for a protein that is encoded by a CYP1B1 gene having a mutation described above. Specific binding of the antibody to the CYP1B1 protein of interest is indicative of a mutation associated with primary congenital glaucoma.

The current invention facilitates identification of certain mutations in the CYP1B1 gene which are associated with primary congenital glaucoma, and thereby facilitates both better and earlier diagnosis and treatment of the disease. Identification of such mutations distinguishes one form of glaucoma from other forms, thereby enabling better treatment planning for affected individuals, as well as for other family members who may be affected individuals or disease carriers.

DETAILED DESCRIPTION OF THE INVENTION

The current invention relates to methods of diagnosing primary congenital glaucoma. As described herein, Applicant has identified certain mutations in the human cytochrome P4501B1 gene (CYP1B1 gene) that are associated with the presence of disease. The CYP1B1 gene is described by Suffer, T. R. el al., *J. Biol. Chem.* 269:13092 (1994), and the genomic structure of the introns and exons of the gene is described by Tang, Y. M. et al, *J. Biol. Chem.* 271:28324 (1996). The entire teachings of these references are incorporated herein by reference. The nucleotide sequence of the CYP1B1 gene is available from GenBank, as accession number UO3688.

The mutations in the CYP1B1 gene, as described herein, include mutations in certain codons of the CYP1B1 gene. The term "codon" indicates a group of three nucleotides which designate a single amino acid in the gene. The codons are numbered from the beginning of the coding sequence of the protein: the first three nucleotides which together designate the initial methionine residue in the protein, together are "codon 1". The CYP1B1 gene has 543 codons, flanked by non-encoding nucleotides. Nucleotides of the introns of the CYP1B1 gene and the non-coding 5' and 3' regions of the CYP1B1 gene are not included in the numbering of the codons. The mutations in the CYP1B1 gene as described herein also include mutations in certain specific nucleotides of the gene. The nucleotide numbering does include non-coding nucleotides (see, e.g., Sutter el al. and the Genbank submission cited supra).

One mutation was a single-base change (a T→C transition) in codon 1. This mutation resulted in a change of the encoded amino acid (the initiation codon (Met1)) to Thr. A second mutation was a single-base change (a G→A transition) in codon 57, resulting in a change of the encoded amino acid from Trp57 to a stop codon, truncating the protein. Several mutations involved amino-acid substitutions in the N-terminal half of the CYP1B1 protein, which is involved in the substrate binding (mutation 3, a single-base change (a C→A transition) in codon 65, resulting in a change of the encoded amino acid from Ala65 to Glu; mutation 4, a single-base change (a T→A transition) in codon 81, resulting in a change of the encoded amino acid from Tyr81 to Asn; mutation 5, a single-base change (a T→G transition) in codon 137, resulting in a change of the encoded amino acid from Tyr137 to Asp; mutation 6, a single-base change (a G→C transition) in codon 238, resulting in a change of the encoded amino acid from Gly238 to Arg; mutation 7, a single-base change (a G→C transition) in codon 242, resulting in a change of the encoded amino acid from Asp242 to His; mutation 8, a single-base change (a C→A transition) in codon 261, resulting in a change of the encoded amino acid from Phe261 to Leu; and mutation 9, a single-base change (a T→G transition) in codon 356, resulting in a change of the encoded amino acid from Val356 to Gly).

Several more mutations involved amino-acid substitutions in the C-terminal half of the CYP1B1 protein that contains the structures involved in heme-binding. These mutations included mutation 10, a single-base change (a G→A transition) in codon 368, resulting in a change of the encoded amino acid from Arg368 to His; mutation 11, a single-base change (a C→T transition) in codon 390, resulting in a change of the encoded amino acid from Arg390 to Cys; mutation 12, a single-base change (a G→A transition) in codon 393, resulting in a change of the encoded amino acid from Ser393 to Asn; mutation 13, a single-base change (a C→T transition) in codon 400, resulting in a change of the encoded amino acid from Pro400 to Ser; mutation 14, a single-base change (a C→G transition) in codon 443, resulting in a change of the encoded amino acid from Ala443 to Gly; mutation 15, a single-base change (a T→A transition) in codon 445, resulting in a change of the encoded amino acid from Phe445 to Ile; mutation 16, a single-base change (a T→C transition) in codon 464, resulting in a change of the encoded amino acid from Ser464 to Pro. In addition, several frame-shift mutations predicted to introduce premature stop codons were identified, including mutation 17, a deletion of nucleotide 4340 (G); mutation 18, a deletion of nucleotide 4634 (T); mutation 19, a deletion of nucleotide 4681 (G); mutation 20, a deletion of nucleotide 8228 (C); and mutation 21, a deletion of nucleotides 8373–8378.

Using methods such as those described herein, or other appropriate methods, it is now possible to diagnose primary congenital glaucoma by detecting a mutation or mutations in the CYP1B1 gene that are associated with glaucoma.

In a first method of diagnosing primary congenital glaucoma, hybridization methods, such as Southern analysis, are used (see *Current Protocols in Molecular Biology,* Ausubel, F. et al., eds., John Wiley & Sons, including all supplements through 1997). For example, a test sample of genomic DNA, RNA, or cDNA, is obtained from an individual suspected of having (or carrying a defect for) primary congenital glaucoma (the "test individual"). The individual can be an adult, child, or fetus. The test sample can be from any source which contains genomic DNA, such as a blood or tissue sample, such as from skin or other organs. In a preferred embodiment, the test sample of DNA is obtained from a fibroblast skin sample, from hair roots, or from cells obtained from the oral cavity (e.g., via mouthwash). In another preferred embodiment, the test sample of DNA is obtained from fetal cells or tissue by appropriate methods, such as by amniocentesis or chorionic villus sampling. The DNA, RNA, or cDNA sample is examined to determine whether one of the mutations described above is present; the presence of the mutation is indicated by hybridization of the CYP1B1 gene in the genomic DNA, RNA, or cDNA to a nucleic acid probe. A "nucleic acid probe", as used herein, can be a DNA probe or an RNA probe. The nucleic acid probe hybridizes to at least one of the mutations described above. A fragment of such a nucleic acid probe can also be used, provided that the fragment hybridizes to the part of the CYP1B1 gene that contains the mutation.

To diagnose primary congenital glaucoma by hybridization, a hybridization sample is formed by contacting the test sample containing the CYP1B1 gene with at least one nucleic acid probe. The hybridization sample is maintained under conditions which are sufficient to allow specific hybridization of the nucleic acid probe to the CYP1B1 gene. "Specific hybridization", as used herein, indicates exact hybridization (e.g., with no mismatches). Specific hybridization can be performed under high stringency conditions or moderate stringency conditions, for example. "Stringency conditions" for hybridization is a term of art which refers to the conditions of temperature and buffer concentration which permit hybridization of a particular nucleic acid to another nucleic acid in which the first nucleic acid may be perfectly complementary to the second, or the first and second nucleic acids may share only some degree of complementarity. For example, certain high stringency conditions can be used which distinguish perfectly complementary nucleic acids from those of less complementarity. "High stringency conditions" and "moderate stringency conditions" for nucleic acid hybridizations are explained in chapter 2.10 and 6.3, particularly on pages 2.10.1–2.10.16 and pages 6.3.1–6 in *Current Protocols in Molecular Biology,* supra, the teachings of which are hereby incorporated by reference. The exact conditions which determine the stringency of hybridization depend on factors such as length of nucleic acids, base composition, percent and distribution of mismatch between the hybridizing sequences, temperature, ionic strength, concentration of destabilizing agents, and other factors. Thus, high or moderate stringency conditions can be determined empirically. In one embodiment, the hybridization conditions for specific hybridization are moderate stringency. In a particularly preferred embodiment, the hybridization conditions for specific hybridization are high stringency.

Specific hybridization, if present, is then detected using standard methods. If specific hybridization occurs between the nucleic acid probe and the CYP1B1 gene in the test sample, then the CYP1B1 gene has a mutation associated with primary congenital glaucoma. More than one nucleic acid probe can also be used concurrently in this method. Specific hybridization of any one of the nucleic acid probes is indicative of a mutation that is associated with primary congenital glaucoma, and is therefore diagnostic for the disease.

For example, in the diagnosis of primary congenital glaucoma, a nucleic acid probe can be prepared that hybridizes to a part of the CYP1B1 gene having a T→C transition in codon 1. If this nucleic acid probe specifically hybridizes with the CYP1B1 gene in the test sample, a diagnosis of primary congenital glaucoma is made. Alternatively, a nucleic acid probe can be prepared that hybridizes to a CYP1B1 gene having one of the other mutations described above. Specific hybridization of such a nucleic acid probe with the CYP1B1 gene in the test sample is indicative of primary congenital glaucoma.

In another hybridization method, Northern analysis (see *Current Protocols in Molecular Biology,* Ausubel, F. et al., eds., John Wiley & Sons, supra) is used to identify the presence of a mutation associated with glaucoma. For Northern analysis, a sample of RNA is obtained from the test individual by appropriate means. Specific hybridization of a nucleic acid probe, as described above, to RNA from the individual is indicative of a mutation that is associated with primary congenital glaucoma, and is therefore diagnostic for the disease.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., Bioconjugate Chemistry, 1994, 5, American Chemical Society, p. 1 (1994). The PNA probe can be designed to specifically hybridize to a CYP1B1 gene having a mutation associated with glaucoma. Hybridization of the PNA probe to the mutant CYP1B1 gene is diagnostic for the disease.

In another method of the invention, mutation analysis by restriction digestion can be used to detect mutations, if the mutation in the gene results in the creation or elimination of a restriction site. A test sample containing genomic DNA is obtained from the test individual. Polymerase chain reaction (PCR) or Ligase chain reaction (LCR) can be used to amplify the CYP1B1 gene (and, if necessary, the flanking sequences) in a test sample of genomic DNA from the test individual. RFLP analysis is conducted as described (see *Current Protocols in Molecular Biology*, supra). The digestion pattern of the relevant DNA fragment indicates the presence or absence of the mutation associated with primary congenital glaucoma.

Sequence analysis can also be used to detect specific mutations in the CYP1B1 gene. A test sample of DNA is obtained from the test individual. PCR or LCR can be used to amplify the gene, and/or its flanking sequences. The sequence of the CYP1B1 gene, or a fragment of the gene, is determined, using standard methods. The sequence of the gene (or gene fragment) is compared with the known nucleic acid sequence of the gene. The presence of any of the mutations associated with glaucoma as described above indicates that the individual is affected with, or is a carrier for, primary congenital glaucoma.

Allele-specific oligonucleotides can also be used to detect the presence of a mutation associated with glaucoma, through the use of dot-blot hybridization of amplified gene products with allele-specific oligonucleotide (ASO) probes (see, for example, Saiki, R. et al., (1986), *Nature* (London) 324:163–166). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to the CYP1B1 gene. An allele-specific oligonucleotide probe that is specific for particular mutations in the CYP1B1 gene can be prepared, using standard methods (see *Current Protocols in Molecular Biology*, supra). To identify the presence or absence of mutations that are associated with glaucoma, a test sample of DNA is obtained from the test individual. PCR or LCR can be used to amplify all or a fragment of the CYP1B1 gene, and its flanking sequences. The DNA containing the amplified CYP1B1 gene (or fragment of the gene) is dot-blotted, using standard methods (see *Current Protocols in Molecular Biology*, supra), and the blot is contacted with the oligonucleotide probe. The presence of specific hybridization of the probe to the amplified CYP1B1 gene is then detected. Specific hybridization of an allele-specific oligonucleotide probe to DNA from the individual is indicative of a mutation in the CYP1B1 gene that is associated with primary congenital glaucoma, and is therefore diagnostic for the disease.

Diagnosis of primary congenital glaucoma can also be made by examining the composition of the protein encoded by the CYP1B1 gene. A test sample from an individual is assessed for the presence of an alteration in the qualitative protein expression (i.e., the composition of the protein), or both. An "alteration" in the protein composition, as used herein, refers to an alteration in composition of CYP1B1 protein in a test sample, as compared with the known composition of the non-mutant CYP1B1 protein (e.g., CYP1B1 protein in a control sample). A control sample is a sample that corresponds to the test sample (e.g., is from the same type of cells), and is from an individual who is not affected by primary congenital glaucoma. An alteration in the composition of the protein in the test sample is indicative of primary congenital glaucoma. Various means of examining the composition of protein encoded by the CYP1B1 gene can be used, including spectroscopy, colorimetry, electrophoresis, isoelectric focusing, and immunoblotting (see *Current Protocols in Molecular Biology*, particularly chapter 10). For example, Western blotting analysis, using an antibody that specifically binds to a protein encoded by CYP1B1 gene having one of the mutations described above, can be used to identify the presence in a test sample of a protein encoded by a mutant CYP1B1 gene. The presence of a protein encoded by a mutant CYP1B1 gene, is diagnostic for glaucoma.

The invention also relates to antibodies to mutant proteins encoded by a CYP1B1 gene having one or more of the mutations described herein. Antibodies can be raised to the mutant protein or fragment of the mutant protein using standard methods (see, for example, *Current Protocols in Molecular Biology*, supra). The term "antibody", as used herein, encompasses both polyclonal and monoclonal antibodies, as well as mixtures of more than one antibody reactive with the protein or protein fragment (e.g., a cocktail of different types of monoclonal antibodies reactive with the mutant protein or protein fragment). The term antibody is further intended to encompass whole antibodies and/or biologically functional fragments thereof, chimeric antibodies comprising portions from more than one species, humanized antibodies, human-like antibodies, and bifunctional antibodies. Biologically functional antibody fragments are those fragments sufficient for binding of the antibody fragment to the mutant protein of interest.

Monoclonal antibodies (mAb) reactive with a mutant protein encoded by a CYP1B1 gene can be produced using somatic cell hybridization techniques (Kohler and Milstein, *Nature* 256:495–497 (1975)) or other techniques). In a typical hybridization procedure, a crude or purified mutant protein encoded by a CYP1B1 gene having one or more of the mutations described herein can be used as the immunogen. An animal is immunized with the immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies to the mutant protein of the invention. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies are produced that are reactive with the mutant protein encoded by the CYP1B1 gene. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Antibodies that specifically bind to a protein or protein fragment encoded by the mutant CYP1B1 gene (i.e., those that bind to the protein or protein fragment encoded by the mutant gene, but not to protein encoded by a non-mutant copy of the gene) can also be used in methods of diagnosis. A test sample containing the protein encoded by the CYP1B1 gene is contacted with the antibody; binding of the antibody to the protein is indicative of the presence of a protein encoded by the mutant gene, and is diagnostic for disease.

The present invention also includes kits useful in the methods of the invention. The kits can include a means for obtaining a test sample; nucleic acid probes, PNA probes, or allele-specific oligonucleotide probes; appropriate reagents;

antibodies to mutant proteins encoded by a CYP1B1 gene having a mutation as described herein; instructions for performing the methods of the invention; control samples; and/or other components. In a preferred embodiment, the kit comprises at least one reagent useful for identifying a mutation in the CYP1B1 gene, and instructions for performing the methods described herein.

The invention is further illustrated by the following Example.

EXAMPLE

Identification of a CYP1B1 Gene Mutations Associated with Primary Congenital Glaucoma Methods used to identify the mutations are described in U.S. Pat. No. 5,830,661 to Sarfarazi. Briefly, for rapid mutation screening, fragments containing portions of the CYP1B1 gene were amplified from genomic DNA with primers, using polymerase chain reaction (PCR), and the PCR products were analyzed on polyacrylamide minigels consisting of 5% Acrylamide/Bis solution (19:1), 15% urea, and 1× TBE. The mutations described herein were either sporadic or familial, and found in one or more individuals or families from varying geographical populations (families of Israeli, United Kingdom, Turkey, United States of America, Bulgaria, Lebanon, and Brazil origin).

The mutations described above are summarized in the Table.

TABLE

Mutations Associated with Primary Congenital Glaucoma

| Mutation | Nucleic Acid Change | Amino Acid Change | Origin | Note |
|---|---|---|---|---|
| 1 | ATG->ACG | Met1->Thr | Israel | Affects initiation codon |
| 2 | TGG->TGA | Trp57->Stop | UK | Hinge Region |
| 3 | GCG->GAG | Ala65->Glu | UK | These mutations are located in the N-terminal half of the protein, which is involved in substrate binding. |
| 4 | TAC->AAC | Tyr81->Asn | UK | |
| 5 | TAC->GAC | Tyr137->Asp | Turkey | |
| 6 | GGC->CGC | Gly238->Arg | UK | |
| 7 | GAC->CAC | Asp242->His | UK | |
| 8 | TTC->TTA | Phe261->Leu | USA | |
| 9 | GTG->GGG | Val356->Gly | UK | |
| 10 | CGT->CAT | Arg368->His | Bulgaria, UK | These mutations located in the C-terminal half of the protein, which contains the structures involved in heme binding. |
| 11 | CGC->TGC | Arg390->Cys | Bulgaria | |
| 12 | AGC->AAC | Ser393->Asn | Turkey | |
| 13 | CCT->TCT | Pro400->Ser | USA | |
| 14 | GCT->GGT | Ala443->Gly | Lebanon | |
| 15 | TTC->ATC | Phe445->Ile | Bulgaria | |
| 16 | TCA->CCA | Ser464->Pro | UK | |
| 17 | 4340 del G | frame-shift | Brazil | premature stop codon |
| 18 | 4634 del T | frame-shift | Brazil | premature stop codon |
| 19 | 4681 del G | frame-shift | UK | premature stop codon |
| 20 | 8228 del c | frame-shift | Lebanon | premature stop codon |
| 21 | del 8373–8378 | frame-shift | UK | premature stop codon |

The relevant teachings of the references cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of diagnosing primary congenital glaucoma, comprising detecting an alteration in composition of human cytochrome P4501B1 protein, wherein the alteration is selected from the group consisting of:

a change of amino acid Met1 to Thr;
a change of amino acid Ala65 to Glu;
a change of amino acid Tyr81 to Asn;
a change of amino acid Tyr137 to Asp;
a change of amino acid Gly238 to Arg;
a change of amino acid Asp242 to His;
a change of amino acid Phe261 to Leu;
a change of amino acid Val356 to Gly;
a change of amino acid Arg368 to His;
a change of amino acid Arg390 to Cys;
a change of amino acid Ser393 to Asn;
a change of amino acid Pro400 to Ser;
a change of amino acid Ala443 to Gly;
a change of amino acid Phe445 to Ile; and
a change of amino acid Ser464 to Pro,
wherein the presence of an alteration in composition of the human cytochrome P4501B1 protein is indicative of primary congenital glaucoma.

* * * * *